(12) United States Patent
Kato et al.

(10) Patent No.: US 11,421,342 B2
(45) Date of Patent: Aug. 23, 2022

(54) METHOD OF DECOMPOSING QUARTZ SAMPLE, METHOD OF ANALYZING METAL CONTAMINATION OF QUARTZ SAMPLE, AND METHOD OF MANUFACTURING QUARTZ MEMBER

(71) Applicant: SUMCO CORPORATION, Tokyo (JP)

(72) Inventors: Hirokazu Kato, Nagasaki (JP); Takashi Muramatsu, Saga (JP)

(73) Assignee: SUMCO CORPORATION, Tokyo (JP)

( * ) Notice: Subject to any disclaimer, the term of this patent is extended or adjusted under 35 U.S.C. 154(b) by 340 days.

(21) Appl. No.: 16/467,766

(22) PCT Filed: Dec. 7, 2017

(86) PCT No.: PCT/JP2017/043899
§ 371 (c)(1),
(2) Date: Jun. 7, 2019

(87) PCT Pub. No.: WO2018/123490
PCT Pub. Date: Jul. 5, 2018

(65) Prior Publication Data
US 2019/0368071 A1 Dec. 5, 2019

(30) Foreign Application Priority Data

Dec. 27, 2016 (JP) .............................. JP2016-254381

(51) Int. Cl.
| | |
|---|---|
| *G01N 1/40* | (2006.01) |
| *C30B 29/06* | (2006.01) |
| *C30B 31/10* | (2006.01) |
| *G01N 31/00* | (2006.01) |
| *G01N 1/28* | (2006.01) |

(52) U.S. Cl.
CPC .............. *C30B 29/06* (2013.01); *C30B 31/10* (2013.01); *G01N 1/28* (2013.01); *G01N 1/4044* (2013.01); *G01N 31/00* (2013.01)

(58) Field of Classification Search
CPC .......... C30B 29/06; C30B 31/10; G01N 1/28; G01N 1/4044; G01N 31/00
See application file for complete search history.

(56) References Cited

U.S. PATENT DOCUMENTS

| | | | | |
|---|---|---|---|---|
| 5,968,259 | A | * 10/1999 | Kemmochi | ............. C03C 1/006 117/2 |
| 2003/0000458 | A1 | * 1/2003 | Marumo | ................. C30B 31/10 117/200 |
| 2004/0232459 | A1 | * 11/2004 | Takayama | ........... H01L 27/1266 257/295 |
| 2009/0095072 | A1 | * 4/2009 | Shimizu | ............. G01N 29/2462 73/32 A |
| 2012/0077290 | A1 | * 3/2012 | Wu | ................... H01L 21/30604 438/14 |
| 2012/0321895 | A1 | * 12/2012 | Ueda | ..................... C01B 33/181 428/402 |

FOREIGN PATENT DOCUMENTS

| | | | | |
|---|---|---|---|---|
| JP | 11-183342 | | 7/1999 | |
| JP | 3274020 | | 4/2002 | |
| JP | 2003202278 | A * | 7/2003 | ............... G01N 1/28 |
| JP | 2012-69855 | | 4/2012 | |

OTHER PUBLICATIONS

European Patent Office, English computer translation of JP2003202278A (Year: 2021).*
International Search Report issued in International Patent Application No. PCT/JP2017/043899, dated Feb. 13, 2018.
International Preliminary Report on Patentability (IPRP) for PCT/JP2017/043899, dated Jul. 11, 2019.
Office Action for Korean App. No. 10-2019-7017301, dated Oct. 20, 2020 (w/ translation).

* cited by examiner

*Primary Examiner* — Matthew J Song
(74) *Attorney, Agent, or Firm* — Greenblum & Bernstein, P.L.C.

(57) ABSTRACT

Provided is a method of decomposing a quartz sample, which includes contacting a liquid in which at least a part of a quartz sample to be analyzed is immersed with a gas generated from a mixed acid to decompose at least a part of the quartz sample, wherein the liquid is a liquid containing at least water; and the mixed acid is a mixed acid of hydrogen fluoride and sulfuric acid, and a mole fraction of sulfuric acid in the mixed acid ranges from 0.07 to 0.40.

18 Claims, No Drawings

METHOD OF DECOMPOSING QUARTZ SAMPLE, METHOD OF ANALYZING METAL CONTAMINATION OF QUARTZ SAMPLE, AND METHOD OF MANUFACTURING QUARTZ MEMBER

CROSS-REFERENCE TO RELATED APPLICATIONS

This application claims the benefit of priority to Japanese Patent Application No. 2016-254381 filed on Dec. 27, 2016, which is expressly incorporated herein by reference in its entirety.

TECHNICAL FIELD

The present invention relates to a method of decomposing a quartz sample, a method of analyzing metal contamination of a quartz sample, and a method of manufacturing a quartz member.

BACKGROUND ART

Quartz has advantages of high heat resistance, excellent durability and the like. Therefore, quartz members are widely used in various fields. For example, in a field of manufacturing a silicon wafer for use as a semiconductor substrate, a quartz crucible is mainly used for a crucible for use in growing a silicon single crystal ingot.

For example, with respect to semiconductor devices, metal contamination of a semiconductor substrate leads to deterioration of device performance. Therefore, for silicon wafers used as a substrate of a semiconductor device, reduction in metal contamination is demanded. However, if a quartz crucible is contaminated with metal, metal contamination is generated also in a silicon single crystal ingot manufactured using the quartz crucible, and, as a consequence, in a silicon wafer cut out and manufactured from the ingot. Accordingly, to provide silicon wafers with reduced metal contamination, it is desirable to analyze metal contamination of a quartz crucible and raw material quartz powder thereof, and, on the basis of the analysis result, to devise a countermeasure (such as a process maintenance work of manufacturing process of manufacturing raw material quartz powder and/or manufacturing process of a quartz crucible) for reducing metal contamination of a quartz crucible.

As described above, analysis of metal contamination of a quartz sample is a way to provide quartz members in which metal contamination has been reduced.

Analysis of metal contamination of solid materials such as quartz is performed, usually, by decomposing a solid material to obtain a decomposed substance (for example, in liquid), and after a pretreatment if necessary, introducing the substance into an analyzer. As a decomposition method, there is a known method in which a solid material to be analyzed is contacted with a decomposition solution to be dissolved and decomposed (liquid phase decomposition method), and a method in which a solid material to be decomposed is contacted with a decomposition gas to be decomposed (vapor phase decomposition method) (see for example Japanese Patent No. 3274020, which is expressly incorporated herein by reference in its entirety.

SUMMARY OF INVENTION

A liquid phase decomposition method tends to show a shorter decomposition time period as compared with a vapor phase decomposition method. Further, with respect to reduction in a decomposition time period, it is also proposed to perform liquid phase decomposition under pressure (also referred to as a pressurized acidolysis method) for facilitating decomposition. However, in the pressurized acidolysis method, use of a pressure-resistant vessel is necessary and, therefore, vessel selection is restricted. Accordingly, if a new decomposition method capable of decomposing a quartz sample in a short time period as is the case for a pressurized acidolysis method can be provided, a process of decomposing a quartz sample may be performed simply.

An aspect of the present invention provides for a new decomposition method for decomposing a quartz sample in a short time period.

An aspect of the present invention relates to a method of decomposing a quartz sample, which includes:

contacting a liquid in which at least a part of a quartz sample to be analyzed is immersed with a gas generated from a mixed acid to decompose at least a part of the quartz sample, wherein the liquid is a liquid containing at least water; and the mixed acid is a mixed acid of hydrogen fluoride and sulfuric acid, and a mole fraction of sulfuric acid in the mixed acid ranges from 0.07 to 0.40.

In an embodiment, a mole fraction of hydrogen fluoride in the mixed acid is equal to or more than 0.27.

In an embodiment, the liquid is hydrofluoric acid.

In an embodiment, the liquid is pure water.

In an embodiment, the decomposition is performed in a sealed vessel.

In an embodiment, the decomposition is performed without pressurization of an inside of the sealed vessel.

In an embodiment, the decomposition is performed without heating of an inside of the sealed vessel.

Another aspect of the present invention relates to a method of analyzing metal contamination of a quartz sample, which includes:

decomposing a quartz sample by the above decomposition method; and analyzing a metal component in a decomposed substance obtained by the decomposition.

Another aspect of the present invention relates to a method of manufacturing a quartz member, which includes:

analyzing quartz powder collected from a quartz powder lot by the above method of analyzing metal contamination; and in a case where a metal contamination level is determined to be an acceptable level by the analysis, producing a quartz member in a process of manufacturing a quartz member using quartz powder contained in the lot.

Another aspect of the present invention relates to a method of manufacturing a quartz member, which includes:

producing a quartz powder lot in a process of manufacturing quartz powder;

analyzing quartz powder collected from the produced quartz powder lot by the above method of analyzing metal contamination;

in a case where a metal contamination level is determined to be an unacceptable level by the analysis, subjecting the process of manufacturing quartz powder to a metal contamination reduction treatment to produce a quartz powder lot in the process of manufacturing quartz powder after this treatment; and producing a quartz member in a process of manufacturing a quartz member using at least a part of quartz powder contained in the produced quartz powder lot.

Another aspect of the present invention relates to a method of manufacturing a quartz member, which includes:

producing a quartz member preliminary body in a process of manufacturing a quartz member;

collecting a part of the produced quartz member preliminary body to analyze the same by the above method of analyzing metal contamination; and in a case where a metal contamination level is determined to be an acceptable level by the analysis, subjecting the quartz member preliminary body to a process of processing the same into a quartz member, or in a case where a metal contamination level is determined to be an unacceptable level by the analysis, subjecting the process of manufacturing a quartz member in which the quartz member preliminary body has been produced to a metal contamination reduction treatment to produce a quartz member preliminary body in the process of manufacturing a quartz member after this treatment, and subjecting the produced quartz member preliminary body to a process of processing the same into a quartz member.

In an embodiment, the quartz member is a quartz crucible.

In an embodiment, the quartz crucible is a crucible for growing a silicon single crystal ingot.

According to an aspect of the present invention, a quartz sample can be decomposed in a short time period similar to that in pressurized acidolysis.

DESCRIPTION OF EMBODIMENTS

[Method of Decomposing Quartz Sample]

An aspect of the present invention relates to a method of decomposing a quartz sample, which includes contacting a liquid in which at least a part of a quartz sample to be analyzed is immersed with a gas generated from a mixed acid to decompose at least a part of the quartz sample, wherein the liquid is a liquid containing at least water; and the mixed acid is a mixed acid of hydrogen fluoride and sulfuric acid, and a mole fraction of sulfuric acid in the mixed acid ranges from 0.07 to 0.40.

According to the above decomposition method, a quartz sample can be decomposed in a short decomposition time period, for example, in a decomposition time period similar to a decomposition time period of a quartz sample by a conventional pressurized acidolysis method. The present inventors guess the reason for making it possible to decompose a quartz sample in a short time period by the above decomposition method as follows.

The above mixed acid is a mixed acid of hydrogen fluoride and sulfuric acid. The present inventors guess that the mixed acid can generate hydrogen fluoride gas (also referred to as "hydrofluoric acid gas (HF gas)") in a short time period, as a consequence of inclusion of sulfuric acid in the mole fraction falling within the above range in hydrogen fluoride. In addition, the present inventors consider that a fact that a gas generated from the mixed acid is absorbed by the above liquid so as to effectively decompose a quartz sample immersed in the liquid also contributes to short-time period decomposition of a quartz sample.

However, the above description is a guess of the present inventors, and does not restrict the present invention at all.

Hereinafter, the above decomposition method will be explained in more detail.

<Quartz Sample>

A quartz sample to be analyzed in the decomposition method may have any shape such as a powder-like, lump-like, rid-like or plate-like shape. The size thereof is also not particularly limited. A quartz sample to be analyzed can be, for example, sample powder obtained by collecting a part of quartz powder to be used as a raw material for a quartz member, a sample piece obtained by collecting a part of a produced quartz member, and the like.

In the present invention and the present description, "quartz" means a solid of silicon dioxide, and the solid can be in a crystalline state, in an amorphous state, or in a mixed state of crystalline and amorphous states. Moreover, in the present invention and the present description, a "quartz sample" means a sample containing quartz as a main component. The main component means a component that accounts for the largest proportion among constituent components. For example, in a quartz sample, quartz can account for from 90 mass % to 100 mass % relative to the entire constituent components. The same can also be applied to "quartz powder" and to a "quartz member".

<Liquid>

The liquid in which at least a part of a quartz sample is to be immersed is a liquid that contains at least water. It is considered that the liquid can absorb effectively a hydrogen fluoride gas generated from the mixed acid by containing at least water. The liquid can be, in an embodiment, pure water. Pure water means water having been subjected to a treatment for eliminating impurities, and preferably can be water whose specific resistance is from 1 to 10 MΩ·cm and/or whose electroconductivity is from 1.0 to 0.1 µS/cm. In the present invention and the present description, "pure water" also includes ultrapure water. Ultrapure water means water whose impurity content is equal to or less than 0.01 µg/L.

In another embodiment, the liquid can be hydrofluoric acid (aqueous solution of hydrogen fluoride). Hydrogen fluoride (HF) concentration in hydrofluoric acid can be, for example, from 30 to 50 mass %. As hydrofluoric acid, use of hydrofluoric acid commercially available as high-purity hydrofluoric acid is preferable. In the present invention and the present description, "high-purity" means that an impurity amount is equal to or less than 0.01 µg/L.

The use of pure water or high-purity hydrofluoric acid as the liquid is preferable from the viewpoint of reducing brought-in contamination from the liquid.

The liquid contacts a gas generated from the mixed gas, in a state where at least a part of a quartz sample to be analyzed is immersed therein. As an example, a usage amount of the liquid per 1 g of a quartz sample can be set ranging from 1 to 5 mL. In contact with the gas, only a part of a quartz sample may be immersed in the liquid, or the whole thereof may be immersed. Moreover, there is such a case that a quartz sample, only a part of which was immersed in the liquid at the start of contact, is wholly immersed in the liquid as a consequence of progress of decomposition. There is also such a case that, in a quartz sample a part of which is immersed in the liquid, a part thereof not immersed in the liquid may contact a gas generated from the mixed acid.

<Mixed Acid>

A mixed acid that generates a gas to be contacted with the liquid is a mixed acid of hydrogen fluoride (HF) and sulfuric acid, in which a mole fraction of sulfuric acid in the mixed acid ranges from 0.07 to 0.40. The present inventors consider that a fact that the mole fraction of sulfuric acid is equal to or more than 0.07 makes it possible to generate effectively hydrogen fluoride gas from the mixed acid in a short time period. From this viewpoint, the mole fraction of sulfuric acid in the mixed acid is preferably equal to or more than 0.10, and more preferably equal to or more than 0.20. In the mixed acid, a greater proportion of sulfuric acid is preferable from the viewpoint of generating hydrogen fluoride gas in a shorter time period. However, if the proportion of sulfuric acid becomes as great as more than 0.40 in mole fraction in the mixed acid, degradation of a vessel due to reaction heat in the reaction of hydrogen fluoride and sulfuric acid and/or deterioration of workability due to rapid gas generation may occur. Taking this into consideration, the mole fraction of sulfuric acid in a mixed acid for use in the decomposition method is equal to or less than 0.40, preferably equal to or less than 0.38, and more preferably equal to or less than 0.35.

In the present invention and the present description, a mole fraction is a value obtained as a value by dividing a mole number of a component whose mole fraction is to be determined by the total mole number of components contained in the mixed acid. In a case where hydrogen fluoride and sulfuric acid, respectively, are to be mixed in a solution state, a mole number of hydrogen fluoride and a mole number of sulfuric acid can be calculated from an equation: mole number=liquid amount×density×concentration/molecular weight. Here for example, a unit of a liquid amount is mL, and a unit of density is g/mL. Solutions for use in preparing the mixed acid may be or may not be a high-purity product. In a case where the total mole number in the mixed acid is to be calculated, impurities in the solution shall not be taken into consideration. As an example, a mole fraction of sulfuric acid in a mixed acid prepared by mixing 700 mL of 50 mass % hydrofluoric acid (aqueous solution of hydrogen fluoride) and 200 mL of a 98 mass % sulfuric acid aqueous solution is calculated as follows.

Mole number of hydrogen fluoride (HF): liquid amount×density×concentration/molecular weight=700×1.19×0.5/19≈21.92 (mole)

Mole number of sulfuric acid ($H_2SO_4$): liquid amount×density×concentration/molecular weight=200×1.84×0.98/98≈3.68 (mole)

Mole number of water (water in hydrofluoric acid+ water in sulfuric acid solution): 700×1.19×0.5/ 18+200×1.84×0.02/18≈23.55

Accordingly, the mole fraction of sulfuric acid is calculated to be 0.07, as follows.

3.68/(21.92+3.68+23.55)≈0.07

In addition, in the above case, the mole fraction of hydrogen fluoride is calculated to be 0.45, as follows.

21.92/(21.92+3.68+23.55)≈0.45

The mixed acid contains hydrogen fluoride with sulfuric acid. From the viewpoint of generating hydrogen fluoride gas in a shorter time period, the mole fraction of hydrogen fluoride in the mixed acid is preferably equal to or more than 0.27, and more preferably equal to or more than 0.30. On the other hand, when workability and the like are taken into consideration, the mole fraction of hydrogen fluoride in the mixed acid is preferably equal to or less than 0.45.

The mixed acid is preferably an aqueous solution. In addition to hydrogen fluoride (HF) and sulfuric acid ($H_2SO_4$), another acid component may not be contained or may be contained, and it is preferably not contained. In other words, acid components contained in the mixed acid preferably consist of hydrogen fluoride and sulfuric acid. A usage amount of the mixed acid is not particularly limited. For example, it can be set to be around from 50 to 1000 mL per 1 g of a quartz sample.

<Decomposition of Quartz Sample>

Decomposition of a quartz sample to be analyzed is performed by contacting a liquid, in which at least a part of a quartz sample is immersed, with a gas generated from the mixed acid. As described above, it is considered that the hydrogen fluoride gas generated from the mixed acid is absorbed by the liquid, which makes it possible to decompose the quartz sample immersed in the liquid having absorbed the hydrogen fluoride gas. A specific embodiment of this decomposition is explained below.

A vessel with a cover (hereinafter, referred to as an "outer vessel") and a vessel with a size to be placed inside the outer vessel (hereinafter, referred to as an "inner vessel) are prepared.

A quartz sample to be analyzed and a liquid containing at least water are charged into the inner vessel. As described above, the whole quartz sample may be immersed in the liquid, or only a part thereof may be immersed.

The inner vessel is arranged into the outer vessel after introduction of the mixed acid therein, or the mixed acid is introduced into the outer vessel after arrangement of the inner vessel so as not to be introduced into the inner vessel, and subsequently the cover of the outer vessel is closed. As a consequence, an inner space of the outer vessel is filled with a gas generated from the mixed acid, and the gas contacts the liquid in the inner vessel. Consequently, decomposition of the quartz sample can proceed.

The above embodiment is an example of performing decomposition of a quartz sample in a sealed vessel. It is preferable to decompose a quartz sample in a sealed vessel for performing effectively the decomposition in a shorter time period. Here, "sealed" is not necessarily limited to a state where a gas inside a sealed vessel is completely prevented from leaking to the outside of the sealed vessel, and leakage of a small amount gas that might occur usually in this field shall be allowed. In the above decomposition method, decomposition of a quartz sample can be progressed effectively by the use of the mixed acid and the liquid, and therefore a quartz sample can be decomposed in a short time period without facilitating the decomposition by pressurization. Accordingly, without pressurizing the inside of the sealed vessel, a quartz sample can be decomposed in a short time period. Due to a similar reason, without heating the inside of the sealed vessel, a quartz sample can be decomposed in a short time period. For performing pressurization, a pressure-resistant vessel is necessary, and for performing heating, a heat-resistant vessel is necessary. Accordingly, a fact that pressurization or heating is unnecessary is preferable from the viewpoint that the decomposition can be performed with less restriction on a vessel. In the above analysis method, for example, various common resin vessels can be used as the outer vessel and the inner vessel. Moreover, for example, in a conventional pressurized acidolysis method, a stainless steel vessel that is a pressure-resistant vessel is sometimes used, but a stainless steel vessel may deteriorate accuracy of the analysis due to disturbance (mixing of a metal component) from the vessel. In contrast, if pressurization is unnecessary, possibility of such disturbance can be reduced or eliminated. In the present invention and the present description, "to perform the decomposition without pressurizing the inside of a sealed vessel" means that the decomposition is performed without raising pressure in the sealed vessel using a pressure controller, and "to perform the decomposition without heating the inside of a sealed vessel" means that the decomposition is performed without raising temperature in the sealed vessel using a temperature controller.

By the decomposition method according to an aspect of the present invention having been explained above, a part of or the whole of a quartz sample can be decomposed.

[Method of Analyzing Metal Contamination of Quartz Sample]

An aspect of the present invention relates to a method of analyzing metal contamination of a quartz sample, which includes decomposing a quartz sample by the above decomposition method; and analyzing a metal component in a decomposed substance obtained by the decomposition.

In the above method of analyzing metal contamination, the method of decomposing a quartz sample is as described above in detail. By using the decomposition method according to an aspect of the present invention, a quartz sample can be decomposed in a short time period.

In the decomposition method according to an aspect of the present invention, decomposed substances of a quartz sample are contained in the above liquid. For example, in a case where an undecomposed quartz sample is left in the liquid, separation thereof by a known separation method such as filtration is preferable. The liquid containing decomposed substances may be subjected as is to metal component analysis, or may be heated with a hot plate or the like to be dried and then collected with a dilute acid solution (recovery liquid), and the collected liquid may be subjected to metal component analysis. The latter embodiment is preferable from the viewpoint of improved analysis sensitivity. In this case, any dilute acid solution can be used without restriction, as far as it is a solution having acid concentration of a level that allows the solution to be introduced into an analyzer for analyzing metal components. Specific examples of dilute acid solutions include hydrofluoric acid (aqueous solution of hydrogen fluoride), aqueous solution of nitric acid and the like, with concentration of equal to or less than several mass % (for example, around from 0.5 to 5 mass %). As an analyzer for analyzing metal components, a known analyzer capable of qualitative analysis and/or quantitative analysis of metal components, such as inductively coupled plasma mass spectrometry (ICP-MS), atomic absorption spectrometry (AAS) and the like, can be used.

In this way, analysis results with respect to various kinds of metal contamination in a quartz sample to be analyzed, such as presence or absence of metal contamination, kinds of contaminating metals and the amount of contaminants, can be obtained. These analysis results can be utilized for making it possible to provide metal members with reduced metal contamination. This point will be described later.

[Method of Manufacturing Quartz Member]

According to an aspect of the present invention, the following method of manufacturing a quartz member is also provided.

A method of manufacturing a quartz member (hereinafter, referred to as a "manufacturing method 1"), which includes:

analyzing quartz powder collected from a quartz powder lot by the above method of analyzing metal contamination; and in a case where a metal contamination level is determined to be an acceptable level by the analysis, producing a quartz member in a process of manufacturing a quartz member using quartz powder contained in the lot.

A method of manufacturing a quartz member (hereinafter, referred to as a "manufacturing method 2"), which includes:

producing a quartz powder lot in a process of manufacturing quartz powder;

analyzing quartz powder collected from the produced quartz powder lot by the above method of analyzing metal contamination;

in a case where a metal contamination level is determined to be an unacceptable level by the analysis, subjecting the process of manufacturing quartz powder to a metal contamination reduction treatment to produce a quartz powder lot in the process of manufacturing quartz powder after this treatment; and producing a quartz member in a process of manufacturing a quartz member using at least a part of quartz powder contained in the produced quartz powder lot.

A method of manufacturing a quartz member (hereinafter, referred to as a "manufacturing method 3"), which includes:

producing a quartz member preliminary body in a process of manufacturing a quartz member;

collecting a part of the produced quartz member preliminary body and analyzing the same by the above method of analyzing metal contamination; and in a case where a metal contamination level is determined to be an acceptable level by the analysis, subjecting the quartz member preliminary body to a process of processing the same into a quartz member, or in a case where a metal contamination level is determined to be an unacceptable level by the analysis, subjecting the process of manufacturing a quartz member in which the quartz member preliminary body has been produced to a metal contamination reduction treatment to produce a quartz member preliminary body in the process of manufacturing a quartz member after this treatment, and subjecting the produced quartz member preliminary body to a process of processing the same into a quartz member.

In an embodiment, a quartz member can be manufactured using quartz powder. In the manufacturing method 1, a quartz member is manufactured using quartz powder for which it has been confirmed that metal contamination is little (at an acceptable level) by the method of analyzing metal contamination according to an aspect of the present invention. In the manufacturing method 2, a quartz member is manufactured using quartz powder produced after suppressing generation of metal contamination due to a process of manufacturing quartz powder, on the basis of an analysis result obtained by the method of analyzing metal contamination according to an aspect of the present invention. In the manufacturing method 3, whether or not quartz powder is to be used, metal contamination due to a process of manufacturing a quartz member is reduced according to need, on the basis of an analysis result obtained by the method of analyzing metal contamination according to an aspect of the present invention. Each of the manufacturing methods 1 to 3 is a manufacturing method capable of providing a quartz member with reduced metal contamination, as a consequence of the use of the method of analyzing metal contamination according to an aspect of the present invention.

Hereinafter, the above manufacturing methods will be explained in more detail.

<Manufacturing Method 1>

In the manufacturing method 1, quartz powder collected from a quartz powder lot is analyzed by the method of analyzing metal contamination according to an aspect of the present invention. For details, the quartz powder is decomposed by the decomposition method according to an aspect of the present invention, and metal components in the obtained decomposed substance are analyzed. A quartz powder lot means an aggregate of quartz powder, and occasionally a number, sign or the like for identifying a lot is given to every lot. An amount of quartz powder to be collected for analysis is not particularly limited. A quartz powder lot may be a commercial product, or may be one manufactured by a known method.

In a case where a metal contamination level is determined to be an acceptable level for quartz powder collected form the quartz powder lot, a quartz member is produced using the whole of or a part of quartz powder in the quartz powder lot. Consequently, a quartz member can be produced using quartz powder for which it has been confirmed that metal contamination is little to make it possible to provide a quartz member with little metal contamination. Here, an acceptable level for metal contamination is not particularly limited, and may be set in accordance with quality demanded for quartz member of finished products, intended use of quartz member of finished products and the like. For example, it can be determined that a metal contamination level is an acceptable level on the basis of a fact that content of one kind of, or contents of two or more kinds of specific metal components are equal to or less than a predetermined value, that a total amount of metal components is equal to or less than a predetermined value, that a specific metal component is not detected by an analyzer, and the like.

Production of a quartz member from quartz powder can be performed by a known manufacturing method, such as a method of melting and molding quartz powder into an intended shape (melt method), in a process of manufacturing a quartz member. For example, when a quartz crucible is taken for an example of a quartz member, a quartz crucible can be produced by arc-melting quartz powder in a rotating mold.

<Manufacturing Method 2>

In the manufacturing method 2, a quartz powder lot is produced in a process of manufacturing quartz powder, and quartz powder collected from a produced quartz powder lot is analyzed by the method of analyzing metal contamination according to an aspect of the present invention. The process of manufacturing quartz powder can be a manufacturing process of manufacturing quartz powder by a known manufacturing method such as a vapor phase method and sol-gel method. The analysis of quartz powder collected from a quartz powder lot produced in the process of manufacturing quartz powder is as described for the manufacturing method 1.

In a case where a metal contamination level for quartz powder collected from the quartz powder lot is determined to be at an acceptable level, it is possible to determine that metal contamination due to the process of manufacturing quartz powder is little. In this case, it is possible to subsequently produce quartz powder in the process of manufacturing quartz powder in which the above quartz powder lot has been produced, and to manufacture a quartz member using the produced quartz powder. On the other hand, in a case where it is determined that a metal contamination level is an unacceptable level for quartz powder collected from the quartz powder lot, it is possible to determine that metal contamination due to the process of manufacturing quartz powder is much. Here, an unacceptable level regarding metal contamination is not particularly limited, and may be set in accordance with quality demanded for a quartz member of finished product, intended use of a quartz member of finished product, and the like. For example, it can be determined that a metal contamination level is an unacceptable level on the basis of a fact that content of one kind of, or contents of two or more kinds of specific metal components are equal to or more than a predetermined value, that a total amount of metal components is equal to or more than a predetermined value, that a specific metal component has been detected by an analyzer, and the like.

In a case where a metal contamination level for quartz powder collected from the above quartz powder lot is determined to be an unacceptable level, the process of manufacturing quartz powder is subjected to a metal contamination reduction treatment, and a quartz powder lot is produced in the process of manufacturing quartz powder after this treatment. Metal contamination reduction treatments can include replacement, cleaning and the like of apparatuses, piping, vessels and the like for use in a process of manufacturing quartz powder. The metal contamination reduction treatments for the process of manufacturing quartz powder in the present invention and the present description include also acquirement of high purity of raw materials (such as raw material gas and raw material solution) for manufacturing quartz powder. As a consequence of giving a metal contamination reduction treatment, it is possible to suppress generation of metal contamination in quartz powder due to a process of manufacturing quartz powder. Accordingly, as a consequence of producing a quartz powder lot in a process of manufacturing quartz powder having been subjected to a metal contamination reduction treatment, and producing a quartz member using the whole of or a part of quartz powder in the produced quartz powder lot, it becomes possible to provide a quartz member in which metal contamination is little. It is also possible to subject quartz powder collected from a quartz powder lot produced after a metal contamination reduction treatment to the method of analyzing metal contamination according to an aspect of the present invention to thereby confirm that a metal contamination level thereof is an acceptable level, and then to subsequently produce a quartz member using the whole of or a part of this quartz powder lot. That is, combination of the manufacturing method 2 and the manufacturing method 1 is also possible. The production of a quartz member from quartz powder in the manufacturing method 2 is as described with respect to the manufacturing method 1.

<Manufacturing Method 3>

In the manufacturing method 3, a quartz member preliminary body is produced in a process of manufacturing a quartz member, and a part of the produced quartz member preliminary body is collected and then analyzed by the method of analyzing metal contamination according to an aspect of the present invention. In the present invention and the present description, a quartz member preliminary body means a substance that will be shipped as a quartz member of finished product by being subjected to process of performing processing into a quartz member. As a consequence of determining a metal contamination level prior to a processing process, preliminary bodies, which should be eliminated as inferior goods because metal contamination thereof is at an unacceptable level, can be extracted and eliminated prior to the processing process. Moreover, as a consequence of giving a treatment for reducing metal contamination due to a process of manufacturing a quartz member to a process of manufacturing a quartz member, it becomes possible to suppress generation of metal contamination in a quartz member due to a process of manufacturing a quartz member.

An embodiment of a process of manufacturing a quartz member is an embodiment of producing a quartz member using quartz powder, as described above. However, the method of manufacturing a quartz member is not limited to an embodiment that uses quartz powder, and may be known manufacturing methods including methods referred to as a direct method, soot method and the like. The direct method is a method of performing synthesis by hydrolyzing a silicon compound such as silicon tetrachloride ($SiCl_4$) in oxyhydrogen flame, and by directly performing accumulation and vitrification. The soot method is a method of manufacturing a synthesized quartz glass according to a following procedure. First, by hydrolyzing a silicon compound such as silicon tetrachloride ($SiCl_4$) in oxyhydrogen flame at lower temperatures (for example around 1100° C.) than that in a direct method to synthesize porous soot of silica. The soot is heat-treated in a suitable gas such as a chloride compound to remove moisture. Finally, the soot is drawn down with rotation at a temperature equal to or higher than about 1500° C. to perform heating and vitrification sequentially from the lower end. A quartz member can be produced by these known manufacturing methods.

A quartz sample to be collected for analysis from a quartz member preliminary body can have any shape such as a power-like, lump-like, rod-like or plate-like shape. The size thereof is also not particularly limited. A quartz sample thus prepared is analyzed by the method of analyzing metal contamination according to an aspect of the present invention. For details, the quartz sample is decomposed by the decomposition method according to an aspect of the present invention, and metal components in the obtained decomposed substance are analyzed. Then, in a case where a metal contamination level is determined to be an acceptable level by this analysis, it is possible to determine that the quartz member preliminary body has little metal contamination, and therefore this quartz member preliminary body is subjected to a processing process in which processing into a quartz member is performed. On the other hand, in a case where a metal contamination level is determined to be an unacceptable level by the analysis, it is possible to determine that the quartz member preliminary body has much metal contamination due to a process of manufacturing a quartz member. In this case, the process of manufacturing a quartz member having produced the quartz member preliminary body is subjected to a metal contamination reduction treatment, then a quartz member preliminary body is produced in the process of manufacturing a quartz member after this treatment, and the produced quartz member preliminary body is subjected to a processing process in which processing into a quartz member is performed.

In this way, a quartz member preliminary body with little metal contamination can be subjected to a processing process, and as a result, it becomes possible to provide a quartz member with little metal contamination as a finished product.

An acceptable level and an unacceptable level in the manufacturing method 3 may be set in accordance with quality demanded for a quartz member of finished product, intended use of a quartz member of finished product, and the like. Details are as those described above with respect to the manufacturing method 1 or 2. Metal contamination reduction treatments for a process of manufacturing a quartz member can include replacement, cleaning and the like of apparatuses, piping, vessels and the like for use in a process of manufacturing quartz member. The metal contamination reduction treatments for the process of manufacturing a quartz member in the present invention and the present description also include acquirement of high purity of raw materials (such as raw material powder, raw material gas and raw material solution, for example) for manufacturing a quartz member. As a consequence of giving a metal contamination reduction treatment, it is possible to suppress generation of metal contamination in a quartz member preliminary body due to a process of manufacturing quartz member. It is also possible to collect a part of a quartz member preliminary body produced after the metal contamination reduction treatment and subject the same to the method of analyzing metal contamination according to an aspect of the present invention to thereby confirm that a metal contamination level thereof falls within an acceptable level, and to subsequently subject the quartz member preliminary body to a processing process in which processing into a quartz member is performed. In a case where a metal contamination level is determined here to be an unacceptable level, a quartz member preliminary body may be produced after additionally performing a metal contamination reduction treatment for a process of manufacturing a quartz member. That is, the determination in the manufacturing method 3 and a metal contamination reduction treatment according to need may be repeated multiple times.

Processing processes for processing a quartz member preliminary body into a quartz member can be known processing processes such as cutting, annealing treatment, polishing and/or cleaning, and include a packing process for shipping finished products.

Quartz members manufactured in the manufacturing methods 1 to 3 having been explained can be quartz members with various shapes and sizes for use in various intended usages. As an example, the quartz member can be a quartz crucible. A quartz crucible is excellent in heat resistance and durability, and therefore is suitable for heating, melting and the like of a substance in the inside thereof. For example, a quartz crucible is widely used as a crucible for growing a silicon single crystal ingot. Reduction in metal contamination in a silicon single crystal ingot is desirable for providing a silicon wafer with reduced metal contamination that brings about deterioration of device performance. For the purpose, it is preferable to suppress generation of metal contamination due to a quartz crucible in a silicon single crystal ingot. According to an aspect of the present invention, as described above, a quartz crucible with reduced metal contamination can be provided, because generation of metal contamination in a quartz member can be suppressed.

EXAMPLES

Hereinafter, the present invention will be further explained with reference to Examples. However, the present invention is not restricted to embodiments represented in Examples. Operations described below were performed under room temperature and atmospheric pressure, unless otherwise noted. As pure water described below, ultrapure water was used.

Example 1

As a quartz sample to be decomposed, 1 g of quartz powder, which had been collected from a quartz powder lot for manufacturing a quartz crucible obtained by a known process of manufacturing quartz powder, was weighed and put into an inner vessel (beaker made of Teflon (registered trade mark)). To this inner vessel, 1.0 mL of 38 mass % high-purity hydrofluoric acid (aqueous solution of hydrogen fluoride) was added.

As an outer vessel, a polypropylene case (longitudinal×width×height=10 cm×20 cm×15 cm) was prepared. Into this outer vessel, 700 ml of 50 mass % hydrofluoric acid (aqueous solution of hydrogen fluoride) and 200 ml of a 98 mass % sulfuric acid aqueous solution were charged, and immediately after that the inner vessel was placed without a cover in the outer vessel and a cover of the outer vessel was closed. They were left to stand so that the mixed solution (mixed acid) of the hydrofluoric acid and sulfuric acid aqueous solution contained in the outer vessel did not enter the inside of the inner vessel and were left keeping at room temperature for 16 hours. In the mixed solution (mixed acid) of the hydrofluoric acid and sulfuric acid aqueous solution contained in the outer vessel, a mole fraction of sulfuric acid is 0.07, and a mole fraction of hydrogen fluoride is 0.45.

After 16 hours, the cover of the outer vessel was opened and quartz powder in the inner vessel was checked to confirm that it was completely decomposed and in a liquid state. That is, it was confirmed that quartz powder had been completely decomposed without pressurization or no heating of the inside of vessel.

After 16 hours, the cover of the outer vessel was opened, and the inner vessel was placed on a hot plate (preset temperature of hot plate: 150° C.) to concentrate and dry a liquid in the inner vessel by heating. A dried substance in the inner vessel was taken in a recovery liquid (2 mass % hydrofluoric acid), and subsequently this recovery liquid was subjected to ICP-MS to perform quantitative analysis of metal components shown in Table 1. Obtained analysis results are shown in Table 1. From the results shown in Table 1, it was confirmed that high-sensitivity analysis of <10 ppt was possible for each metal component.

TABLE 1

| | Li | Na | Al | Fe | Ni | Cu |
|---|---|---|---|---|---|---|
| | | | | Unit: ppb (By mass) | | |
| Example 1 | $4.9 \times 10^2$ | 85 | $8.7 \times 10^4$ | $1.1 \times 10^2$ | 1.2 | 3.7 |

Comparative Example 1

From the quartz powder lot from which quartz powder decomposed in Example 1 had been collected, 1 g of quartz powder was weighed as a quartz sample to be decomposed and was decomposed by a pressurized acidolysis method described below.

The above quartz powder 1 was put into a beaker made of Teflon (registered trade mark). Into the beaker, 3 mL of pure water, 10 mL of 50 mass % hydrofluoric acid, and 3 mL of a 69.5 mass % nitric acid aqueous solution were charged and a cover was closed.

This beaker made of Teflon (registered trade mark) was placed in a stainless steel vessel, and then a cover of the stainless steel vessel was closed. This stainless steel vessel was put into a constant-temperature container kept at 140° C. This system was left for 16 hours in a state where the inside of the stainless steel vessel was pressurized with a reaction gas from the quartz powder, and vapor generated from hydrofluoric acid and the nitric acid aqueous solution.

After 16 hours, the cover of the stainless steel vessel was opened, the cover of the beaker made of Teflon (registered trade mark) was opened, and the inside of the beaker made of Teflon (registered trade mark) was checked to confirm that quartz powder had been completely decomposed.

From the comparison between Example 1 and Comparative Example 1, it was confirmed that the quartz sample could have been decomposed in Example 1 in a similar time period to that in a pressurized acidolysis method (Comparative Example 1).

Examples 2 to 5, Comparative Examples 2 and 3

As a quartz sample to be decomposed, 4 g of quartz powder collected from a quartz powder lot for manufacturing a quartz crucible, which had been obtained by a known process of manufacturing quartz powder, was weighed and put into an inner vessel (beaker made of Teflon (registered trade mark)). To this inner vessel, 38 mass % high-purity hydrofluoric acid (aqueous solution of hydrogen fluoride) was added in amounts shown in Table 2 in Examples 2 to 5. In Comparative Examples 2 and 3, high-purity hydrofluoric acid was not added to the inner vessel.

As an outer vessel, a polypropylene case (longitudinal×width×height=10 cm×20 cm×15 cm) was prepared. Into this outer vessel, 700 ml of 50 mass % hydrofluoric acid (aqueous solution of hydrogen fluoride) and a 98 mass % sulfuric acid aqueous solution each in a liquid amount shown in Table 2 were charged, and immediately after that the inner vessel was placed without a cover in the outer vessel and a cover of the outer vessel was closed. They were left to stand so that the mixed solution (mixed acid) of the hydrofluoric acid and sulfuric acid aqueous solution contained in the outer vessel did not enter the inside of the inner vessel and were left keeping at room temperature for 16 hours.

The cover of the outer vessel was opened after 16 hours, the inner vessel was taken out, and a liquid in the inner vessel was filtrated to separate a solid substance (that is, undecomposed quartz powder) and mass of the substance was measured. Each value obtained by subtracting the measured mass from the quartz powder amount (4 g) put into the inner vessel is shown as a decomposed amount in Table 2. A larger decomposed amount means that decomposition speed of a quartz sample is faster and the decomposition has progressed more.

TABLE 2

| | In inner vessel Addition amount (mL), hydrofluoric acid | Mixed acid in outer vessel | | | | |
|---|---|---|---|---|---|---|
| | | Sulfuric acid | | Hydrogen fluoride | | |
| | | Liquid amount, aq. sulfuric acid | Mole fraction of sulfuric acid in mixed acid | Liquid amount, hydrofluoric acid | Mole fraction of hydrogen fluoride in mixed acid | Decomposed amount (g) |
| Comparative Example 2 | 0 | 200 mL | 0.07 | 700 mL | 0.45 | 1.01 |
| Comparative Example 3 | 0 | 1100 mL | 0.30 | 700 mL | 0.32 | 1.09 |
| Example 2 | 1.0 | 200 mL | 0.07 | 700 mL | 0.45 | 1.39 |
| Example 3 | 5.0 | 200 mL | 0.07 | 700 mL | 0.45 | 1.55 |
| Example 4 | 1.0 | 1100 mL | 0.30 | 700 mL | 0.32 | 2.30 |
| Example 5 | 5.0 | 1100 mL | 0.30 | 700 mL | 0.32 | 4 (Completely decompose) |

From the results shown in Table 2, it can be confirmed that decomposition was facilitated, that is, decomposition in a shorter time period was possible in Examples 2 to 4 in which a quartz sample had been charged into the inner vessel with a liquid (hydrofluoric acid) as compared with Comparative Examples 2 and 3 in which no liquid had been charged into the inner vessel.

Examples 6 to 9, Comparative Examples 4 and 5

As a quartz sample to be decomposed, 4 g of quartz powder collected from a quartz powder lot for manufacturing a quartz crucible, which had been obtained by a known process of manufacturing quartz powder, was weighed and put into an inner vessel (beaker made of Teflon (registered trade mark)). To this inner vessel, 1.0 mL of 38 mass % high-purity hydrofluoric acid (aqueous solution of hydrogen fluoride) was added. As an outer vessel, a polypropylene case (longitudinal×width×height=10 cm×20 cm×15 cm) was prepared. Into this outer vessel, 700 ml of 50 mass % hydrofluoric acid (aqueous solution of hydrogen fluoride) and a 98 mass % sulfuric acid aqueous solution each in a liquid amount shown in Table 3 were charged, and immediately after that the inner vessel was placed without a cover in the outer vessel and a cover of the outer vessel was closed. They were left to stand so that the mixed solution (mixed acid) of the hydrofluoric acid and sulfuric acid aqueous solution contained in the outer vessel did not enter the inside of the inner vessel and were left keeping at room temperature for 16 hours.

The cover of the outer vessel was opened after 16 hours, the inner vessel was taken out, and a liquid in the inner vessel was filtrated to separate a solid substance (that is, undecomposed quartz powder) and mass of the substance was measured. Each value obtained by subtracting the measured mass from the quartz powder amount (4 g) put into the inner vessel is shown as a decomposed amount in Table 3, with the results in Example 2 shown in Table 2.

From the results shown in Table 3, it can be confirmed that decomposition was facilitated, that is, decomposition in a shorter time period was possible in Examples 2, 6 to 9 in which a mole fraction of sulfuric acid in the mixed acid in the outer vessel ranged from 0.07 to 0.40 as compared with Comparative Examples 4 and 5 in which the mole fraction in the mixed acid in the outer vessel lied outside the above range.

Examples 10 to 13

As a quartz sample to be decomposed, 4 g of quartz powder collected from a quartz powder lot for manufacturing a quartz crucible, which had been obtained by a known process of manufacturing quartz powder, was weighed and put into an inner vessel (beaker made of Teflon (registered trade mark)). To this inner vessel, pure water was added each in an amount shown in Table 4 in Examples 10 to 13.

As an outer vessel, a polypropylene case (longitudinal× width×height=10 cm×20 cm×15 cm) was prepared. Into this outer vessel, 700 ml of 50 mass % hydrofluoric acid (aqueous solution of hydrogen fluoride) and a 98 mass % sulfuric acid aqueous solution each in a liquid amount shown in Table 4 were charged, and immediately after that the inner vessel was placed without a cover in the outer vessel and a cover of the outer vessel was closed. They were left to stand so that the mixed solution (mixed acid) of the hydrofluoric acid and sulfuric acid aqueous solution contained in the outer vessel did not enter the inside of the inner vessel and were left keeping at room temperature for 16 hours.

The cover of the outer vessel was opened after 16 hours, the inner vessel was taken out, and a liquid in the inner vessel was filtrated to separate a solid substance (that is, undecomposed quartz powder) and mass of the substance was measured. Each value obtained by subtracting the measured mass from the quartz powder amount (4 g) input into the inner vessel is shown as a decomposed amount in Table 4, with the results in Comparative Examples 2 and 3 for comparison.

TABLE 3

| | Mixed acid in outer vessel | | | | |
| --- | --- | --- | --- | --- | --- |
| | Sulfuric acid | | Hydrogen fluoride | | |
| | Liquid amount, aq. sulfuric acid | Mole fraction of sulfuric acid in mixed acid | Liquid amount, hydrofluoric acid | Mole fraction of hydrogen fluoride in mixed acid | Decomposed amount (g) |
| Comparative Example 4 | 0 mL | 0 | 700 mL | 0.49 | 0.444 |
| Comparative Example 5 | 100 mL | 0.04 | 700 mL | 0.47 | 0.866 |
| Example 2 | 200 mL | 0.07 | 700 mL | 0.45 | 1.39 |
| Example 6 | 300 mL | 0.11 | 700 mL | 0.43 | 1.38 |
| Example 7 | 500 mL | 0.17 | 700 mL | 0.40 | 3.04 |
| Example 8 | 1100 mL | 0.30 | 700 mL | 0.32 | 2.30 |
| Example 9 | 1800 mL | 0.40 | 700 mL | 0.27 | 2.32 |

TABLE 4

| | In inner vessel | Mixed acid in outer vessel | | | | |
|---|---|---|---|---|---|---|
| | | Sulfuric acid | | Hydrogen fluoride | | |
| | Addition amount (mL), pure water | Liquid amount, aq. sulfruic acid | Mole fraction of sulfuric acid in mixed acid | Liquid amount, hydrofluoric acid | Mole fraction of hydrogen fluoride in mixed acid | Decomposed amount (g) |
| Comparative Example 2 | 0 | 200 mL | 0.07 | 700 mL | 0.45 | 1.01 |
| Comparative Example 3 | 0 | 1100 mL | 0.30 | 700 mL | 0.32 | 1.09 |
| Example 10 | 1.0 | 200 mL | 0.07 | 700 mL | 0.45 | 1.32 |
| Example 11 | 5.0 | 200 mL | 0.07 | 700 mL | 0.45 | 1.45 |
| Example 12 | 1.0 | 1100 mL | 0.30 | 700 mL | 0.32 | 2.19 |
| Example 13 | 5.0 | 1100 mL | 0.30 | 700 mL | 0.32 | 3.26 |

From the results shown in Table 4, it can be confirmed that decomposition was facilitated, that is, decomposition was possible in a shorter time period in Examples 10 to 13 in which a quartz sample had been charged with a liquid (pure water) in the inner vessel as compared with Comparative Examples 2 and 3 in which no liquid had been charged into the inner vessel.

[Study on Analysis Sensitivity]

<Test 1>

To an inner vessel (beaker made of Teflon (registered trade mark)), 1.0 mL of 38 mass % high-purity hydrofluoric acid (aqueous solution of hydrogen fluoride) was added. No quartz sample was put into the inner vessel.

As an outer vessel, a polypropylene case (longitudinal×width×height=10 cm×20 cm×15 cm) was prepared. Into the outer vessel, 700 ml of 50 mass % hydrofluoric acid (aqueous solution of hydrogen fluoride) and 200 ml of a 98 mass % sulfuric acid aqueous solution were charged, and immediately after that the inner vessel was placed without a cover in the outer vessel and a cover of the outer vessel was closed. They were left to stand so that the mixed solution (mixed acid) of the hydrofluoric acid and sulfuric acid aqueous solution contained in the outer vessel did not enter the inside of the inner vessel and were left keeping at room temperature for 16 hours.

After 16 hours, the cover of the outer vessel was opened, and the inner vessel was placed on a hot plate (preset temperature of hot plate: 150° C.) to concentrate and dry a liquid in the inner vessel by heating. A dried substance in the inner vessel was taken in a recovery liquid (2 mass % hydrofluoric acid), and subsequently this recovery liquid was subjected to ICP-MS to perform analysis of metal components.

The above operation was performed 6 times. Obtained analysis results are shown in Table 5.

<Test 2 (Comparative Test)>

3 mL of pure water, 10 mL of 50 mass % hydrofluoric acid, and 3 mL of a 69.5 mass % nitric acid aqueous solution were put into a beaker made of Teflon (registered trade mark) and a cover was closed.

The beaker made of Teflon (registered trade mark) was placed in a stainless steel vessel, and then a cover of the stainless steel vessel was closed. This stainless steel vessel was put into a constant-temperature container kept at 140° C. This system was left for 16 hours in a state where the inside of the stainless steel vessel was pressurized with a reaction gas from quartz powder, and vapor generated from hydrofluoric acid and nitric acid aqueous solution.

After 16 hours, the cover of the stainless steel vessel was opened, the cover of the beaker made of Teflon (registered trade mark) was opened and the beaker made of Teflon (registered trade mark) was placed on a hot plate (preset temperature of hot plate: 150° C.) to concentrate and dry a liquid in the beaker made of Teflon (registered trade mark) by heating. A dried substance in the beaker made of Teflon (registered trade mark) was taken in a recovery liquid (2 mass % hydrofluoric acid), and subsequently this recovery liquid was subjected to ICP-MS to perform analysis of metal components.

The above operation was performed 6 times. Obtained analysis results are shown in Table 5.

Analysis results of metal components obtained in Tests 1 and 2 are shown in Table 5.

TABLE 5

| | | Li | Na | Al | Fe | Ni | Cu |
|---|---|---|---|---|---|---|---|
| Test 1 | 1st | <1.0 | 2.1 | 1.3 | 3.9 | 1.4 | <1.0 |
| | 2nd | <1.0 | 3.4 | 3.1 | 1.9 | <1.0 | <1.0 |
| | 3rd | <1.0 | 1.9 | 2.5 | 2.1 | <1.0 | <1.0 |
| | 4th | <1.0 | <1.0 | 1.2 | 3.1 | 1.1 | <1.0 |
| | 5th | <1.0 | 1.3 | 3.6 | 2.9 | 1.3 | <1.0 |
| | 6th | <1.0 | 1.5 | 3.1 | 1.8 | <1.0 | <1.0 |
| Test 2 (Test for comparison) | 1st | 10.2 | 174.4 | 233.4 | 628.5 | 71.8 | 1.2 |
| | 2nd | <1.0 | 152.5 | 960.7 | 387.0 | 50.7 | <1.0 |
| | 3rd | 5.2 | 388.7 | 602.6 | 419.8 | 57.4 | 4.2 |
| | 4th | 18.1 | 174.7 | 456.7 | 713.0 | 90.5 | 7.8 |
| | 5th | <1.0 | 287.9 | 901.7 | 2225.9 | 90.7 | 6.4 |
| | 6th | 3.0 | 148.0 | 770.8 | 1633.5 | 122.8 | 5.0 |

In a conventional pressurized acidolysis method, sometimes a stainless steel vessel that is a pressure-resistant vessel is used. However, as shown in Table 5, in Test 2 in which a stainless steel vessel was used, a detection amount of metal components was remarkably large as compared with that in Test 1. It is considered that this is due to mixing of metal components from the stainless steel vessel.

In contrast, the decomposition method according to an aspect of the present invention can be performed without pressurization, and therefore can be performed without the use of a stainless steel vessel. Consequently, a quartz sample can be decomposed without a disturbance (mixing of metal component) on a decomposed substance or a liquid containing a decomposed substance from a stainless steel vessel. This leads metal contamination analysis of a quartz sample to be performed with higher sensitivity, which is preferable.

An aspect of the present invention is useful in manufacturing fields of various quartz members.

The invention claimed is:

1. A method of decomposing a quartz sample, which comprises:
    contacting a liquid in which at least a part of a quartz sample to be analyzed is immersed with a gas generated from a mixed acid to decompose at least a part of the quartz sample,
    wherein
    the liquid is a liquid comprising at least water; and
    the mixed acid is a mixed acid consisting of hydrogen fluoride and sulfuric acid, and
    a mole fraction of sulfuric acid in the mixed acid ranges from 0.07 to 0.40.

2. The method of decomposing a quartz sample according to claim 1, wherein a mole fraction of hydrogen fluoride in the mixed acid is equal to or more than 0.27.

3. The method of decomposing a quartz sample according to claim 1, wherein the liquid is hydrofluoric acid.

4. The method of decomposing a quartz sample according to claim 1, wherein the liquid is water having a specific resistance of from 1 to 10 MΩ·cm and/or an electroconductivity of from 1.0 to 0.1 µS/cm.

5. The method of decomposing a quartz sample according to claim 1, wherein the decomposition is performed in a sealed vessel.

6. The method of decomposing a quartz sample according to claim 5, wherein the decomposition is performed without pressurization of an inside of the sealed vessel.

7. The method of decomposing a quartz sample according to claim 5, wherein the decomposition is performed without heating of an inside of the sealed vessel.

8. A method of analyzing metal contamination of a quartz sample, which comprises:
    decomposing a quartz sample by the method according to claim 1; and
    analyzing a metal component in a decomposed substance obtained by the decomposition.

9. A method of manufacturing a quartz member, which comprises:
    analyzing quartz powder collected from a quartz powder lot by the method according to claim 8; and
    in a case where a metal contamination level is determined to be an acceptable level by the analysis, producing a quartz member in a process of manufacturing a quartz member using quartz powder contained in the lot.

10. The method of manufacturing a quartz member according to claim 9, wherein the quartz member is a quartz crucible.

11. The method of manufacturing a quartz member according to claim 10, wherein the quartz crucible is a crucible for growing a silicon single crystal ingot.

12. A method of manufacturing a quartz member, which comprises:
    producing a quartz powder lot in a process of manufacturing quartz powder;
    analyzing quartz powder collected from the produced quartz powder lot by the method according to claim 8;
    in a case where a metal contamination level is determined to be an unacceptable level by the analysis, subjecting the process of manufacturing quartz powder to a metal contamination reduction treatment to produce a quartz powder lot in the process of manufacturing quartz powder after the treatment; and
    producing a quartz member in a process of manufacturing a quartz member using at least a part of quartz powder contained in the produced quartz powder lot.

13. The method of manufacturing a quartz member according to claim 12, wherein the quartz member is a quartz crucible.

14. The method of manufacturing a quartz member according to claim 13, wherein the quartz crucible is a crucible for growing a silicon single crystal ingot.

15. A method of manufacturing a quartz member, which comprises:
    producing a quartz member preliminary body in a process of manufacturing a quartz member;
    collecting a part of the produced quartz member preliminary body to analyze the part of the produced quartz member preliminary body by the method according to claim 8; and
    in a case where a metal contamination level is determined to be an acceptable level by the analysis, subjecting the quartz member preliminary body to a process of processing the quartz member preliminary body into a quartz member, or
    in a case where a metal contamination level is determined to be an unacceptable level by the analysis,
        subjecting the process of manufacturing a quartz member in which the quartz member preliminary body has been produced to a metal contamination reduction treatment to produce a quartz member preliminary body in the process of manufacturing a quartz member after the treatment, and
        subjecting the produced quartz member preliminary body to a process of processing the produced quartz member preliminary body into a quartz member.

16. The method of manufacturing a quartz member according to claim 15, wherein the quartz member is a quartz crucible.

17. The method of manufacturing a quartz member according to claim 16, wherein the quartz crucible is a crucible for growing a silicon single crystal ingot.

18. The method according to claim 1, wherein:
    the mixed acid is introduced into an outer vessel; and
    the quartz sample to be analyzed and the liquid comprising at least water are charged into an inner vessel, the inner vessel having a size so that the inner vessel can be placed inside the outer vessel.

* * * * *